US012780794B2

(12) United States Patent
Chen et al.

(10) Patent No.: US 12,780,794 B2
(45) Date of Patent: Nov. 3, 2026

(54) GLYCINE N-METHYLTRANSFERASE SPECIFIC ENHANCER AND PREPARATION METHOD AND USES THEREOF

(71) Applicant: KAOHSIUNG MEDICAL UNIVERSITY, Kaohsiung City (TW)

(72) Inventors: Yi-Ming Chen, Kaohsiung City (TW); Cherng-Chyi Tzeng, Kaohsiung City (TW); Yeh-Long Chen, Kaohsiung City (TW); Chih-Hua Tseng, Kaohsiung City (TW); Chia-Hung Yen, Kaohsiung City (TW); Rajni Kant, Kaohsiung City (TW); Ming-Hui Yang, Kaohsiung City (TW)

(73) Assignee: KAOHSIUNG MEDICAL UNIVERSITY, Kaohsiung City (TW)

( * ) Notice: Subject to any disclaimer, the term of this patent is extended or adjusted under 35 U.S.C. 154(b) by 916 days.

(21) Appl. No.: 17/904,607

(22) PCT Filed: Dec. 25, 2020

(86) PCT No.: PCT/CN2020/139547

§ 371 (c)(1),
(2) Date: Sep. 13, 2023

(87) PCT Pub. No.: WO2022/134043

PCT Pub. Date: Jun. 30, 2022

(65) Prior Publication Data

US 2024/0239765 A1 Jul. 18, 2024

(51) Int. Cl.
*C07D 401/12* (2006.01)
*A61K 31/444* (2006.01)
*A61P 35/00* (2006.01)

(52) U.S. Cl.
CPC .......... *C07D 401/12* (2013.01); *A61K 31/444* (2013.01); *A61P 35/00* (2018.01)

(58) Field of Classification Search
CPC ...... C07D 401/12; A61P 35/00; A61K 31/444
USPC .......................................................... 514/332
See application file for complete search history.

(56) References Cited

FOREIGN PATENT DOCUMENTS

| | | | |
|---|---|---|---|
| CN | 103880707 | 6/2014 | |
| WO | WO-2009013163 A1 * | 1/2009 | ............. C11D 3/168 |
| WO | WO-2009017589 A2 * | 2/2009 | ........... G02B 6/4249 |
| WO | WO2018017589 | 1/2018 | |

OTHER PUBLICATIONS

Madany et al., Discoveries (Craiova) Dec. 31, 2018; 6(4) (Year: 2018).*

Ashikari et al., Abstract Oncogene, Nov. 9, 2017;36(45):6272-6281. doi: 10.1038/onc.2017.225. Epub Jul. 10, 2017. (Year: 2017).*

Singh et al. "Synthesis, molecular structure, spectral analysis and cytotoxic activity of two new aroylhydrazones" Journal of Molecular Structure 1135 (2017) 82-97.

Yen et al. "Functional Characterization of Glycine N-Methyltransferase and Its Interactive Protein DEPDC6/DEPTOR in Hepatocellular Carcinoma" Molecular Medicine 18:286; 2012; 286-296.

Kane et al."Synthesis And Characterization of Novel M(II) (M=Mn(II). Ni(II). Cu(II) or Zn(II)) Complexes With Tridentate N2, 0-Donor Ligand (E)-2-Amino-N' -[1-(Pyridin-2-yl)Ethylidene] Benzohydrazide," Bull. Chern. Soc. Ethiop., vol. 30, No. 1, Dec. 31, 2016 (Dec. 31, 2016), pp. 101-110.

Gupta et al. "Stress granule-associated protein G3BP2 regulates breast tumor initiation" PNAS, vol. 114, No. 5, Jan. 31, 2017 (Jan. 31, 2017), pp. 1033-1038.

Cheng et al. "Synthesis, Characterization and Crystal Structures of 3-Hydroxy-N'-[methyl(2-pyridyl)methylene]-2-naphthohydrazide monohydrate and 3-Hydroxy-N'-(3, 5-dibromo-2-hydroxybenzylidene)-2-naphthohydrazide dimethylformamide solvate" J. Chern. Crystallogr., vol. 42, Feb. 28, 2012 (Feb. 28, 2012) pp. 668-672.

* cited by examiner

*Primary Examiner* — Kortney L. Klinkel
*Assistant Examiner* — Grace Ching Hsu
(74) *Attorney, Agent, or Firm* — Timothy H. Van Dyke; Wolter Van Dyke Davis, PLLC

(57) ABSTRACT

The present invention relates to a nicotinohydrazide derivative, a stereoisomer thereof or a pharmaceutically acceptable salt thereof having a structure of formula (I):

(I)

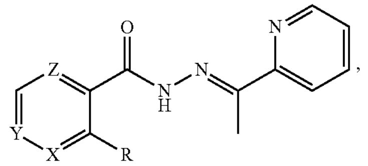

wherein each of X, Y and Z is one of N and CH, at least one of X, Y and Z is CH, at least one of X, Y and Z is N, and R is one of OH and $NH_2$.

5 Claims, 19 Drawing Sheets

Specification includes a Sequence Listing.

K-117

K102

K-90

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial sequence
<220> FEATURE:
<223> OTHER INFORMATION: TBP forward primer

<400> SEQUENCE: 1

tgcacaggag ccaagagtga a                                              21


<210> SEQ ID NO 2
<211> LENGTH: 20
<212> TYPE: DNA
<213> ORGANISM: Artificial sequence
<220> FEATURE:
<223> OTHER INFORMATION: TBP reverse primer

<400> SEQUENCE: 2

cacatcacag ctccccacca                                                20


<210> SEQ ID NO 3
<211> LENGTH: 22
<212> TYPE: DNA
<213> ORGANISM: Artificial sequence
<220> FEATURE:
<223> OTHER INFORMATION: MYC forward primer

<400> SEQUENCE: 3

ttcggttgtt gctgatctgt ct                                             22


<210> SEQ ID NO 4
<211> LENGTH: 21
<212> TYPE: DNA
<213> ORGANISM: Artificial sequence
<220> FEATURE:
```

```
<223> OTHER INFORMATION: MYC reverse primer

<400> SEQUENCE: 4

ccctccactc ggaaggacta t                                               21


<210> SEQ ID NO 5
<211> LENGTH: 18
<212> TYPE: DNA
<213> ORGANISM: Artificial sequence
<220> FEATURE:
<223> OTHER INFORMATION: p21 forward primer

<400> SEQUENCE: 5

tgagccgcga ctgtgatg                                                   18


<210> SEQ ID NO 6
<211> LENGTH: 23
<212> TYPE: DNA
<213> ORGANISM: Artificial sequence
<220> FEATURE:
<223> OTHER INFORMATION: p21 reverse primer

<400> SEQUENCE: 6

gtctcggtga caaagtcgaa gtt                                             23


<210> SEQ ID NO 7
<211> LENGTH: 25
<212> TYPE: DNA
<213> ORGANISM: Artificial sequence
<220> FEATURE:
<223> OTHER INFORMATION: p27 forward primer

<400> SEQUENCE: 7

tgcaaccgac gattcttcta ctcaa                                           25


<210> SEQ ID NO 8
<211> LENGTH: 29
<212> TYPE: DNA
<213> ORGANISM: Artificial sequence
<220> FEATURE:
<223> OTHER INFORMATION: p27 reverse primer

<400> SEQUENCE: 8

caagcagtga tgtatctgat aaacaagga                                       29


<210> SEQ ID NO 9
<211> LENGTH: 19
<212> TYPE: DNA
<213> ORGANISM: Artificial sequence
<220> FEATURE:
<223> OTHER INFORMATION: GNMT forward primer

<400> SEQUENCE: 9

actggatgac tctggacaa                                                  19


<210> SEQ ID NO 10
<211> LENGTH: 17
<212> TYPE: DNA
<213> ORGANISM: Artificial sequence
<220> FEATURE:
<223> OTHER INFORMATION: GNMT reverse primer

<400> SEQUENCE: 10

actgaggatg tggtcgt                                                    17
```

-continued

```
<210> SEQ ID NO 11
<211> LENGTH: 21
<212> TYPE: RNA
<213> ORGANISM: Artificial sequence
<220> FEATURE:
<223> OTHER INFORMATION: MYC-lentiviral shRNA

<400> SEQUENCE: 11

cctgagacag atcagcaaca a                                              21
```

GLYCINE N-METHYLTRANSFERASE SPECIFIC ENHANCER AND PREPARATION METHOD AND USES THEREOF

REFERENCE TO A SEQUENCE LISTING SUBMITTED VIA EFS-WEB

The content of the ASCII text file of the sequence listing named 0136534.seq.app.txt, which is 1.9 KB in size was created on Aug. 18, 2022 and electronically submitted via EFS-Web herewith, the application is incorporated herein by reference in its entirety.

FIELD OF THE INVENTION

The present invention relates to a pharmaceutical composition for inhibiting cancer cells, specifically to a pharmaceutical composition for inhibiting cancer cells through enhancing Glycine N-methyltransferase (GNMT) expression.

BACKGROUND OF THE INVENTION

Hepatocellular carcinoma (HCC) is a global health burden with increasing incidence. Liver cancer is the fifth most common cancer worldwide and the third most common cause of cancer mortality. Because of the late diagnosis, poor treatment options and high recurrence, the incidence of HCC still nearly equals to its mortality rate. Treatment options for HCC are not a lot. Currently, the drugs that have been approved by the Food and Drug Administration (FDA) for HCC treatment are sorafenib and regorafenib. These drugs can only work in some individuals, but they have side effect and patients quickly develop drug resistance. Therefore, there is a high unmet need for HCC. The pace of new drug for HCC is very slow and many compounds failed in clinical trial. The developments of preventive agents, novel therapy or drug combination strategies are urgently needed to improve the patient's survival rate or help the patients to control disease.

GNMT is a tumor suppressor gene (TSG) for HCC. GNMT includes 1-3% of the cytosolic proteins in normal mammalian livers, while it is down regulated in more than 75% HCC patients. GNMT is one of the major enzymes in one-carbon metabolism pathway. It affects genetic stability by regulating the ratio of S-adenosylmethionine to S-adenosylhomocysteine, and serves as the major folate-binding protein in hepatocytes. In addition, a previous study suggested that GNMT is an example of a moonlighting protein. GNMT is able to switch its function from acting as a metabolic enzyme to being a 4S polycyclic aromatic hydrocarbons (PAH) binding protein based on its phosphorylation state, which changes the subunit configuration. By changing the cellular localization of GNMT from the cytoplasm to the nucleus, GNMT is able to act as a transcription cofactor and regulate the expression of detoxification (and/or other target) genes.

Previously, it was found in a $GNMT^{-/-}$ mouse model that both male and female $GNMT^{-/-}$ mice developed chronic hepatitis at the age of 4-11 weeks. These $GNMT^{-/-}$ mice were followed up until 24 months old and the results showed that all female and half of male $GNMT^{-/-}$ mice developed HCC. By contrast, re-expression of GNMT inhibits cell proliferation in cancer cells. On top of that, transgenic mice overexpressing GNMT prevent the carcinogenicity and liver cancer progression induced by aflatoxin B1 (AFB1). More importantly, it was demonstrated that GNMT reduced the proliferation of Huh7 cells and sensitized them to rapamycin treatment both in vitro and in vivo. Recently, it was further demonstrated that the overexpression of GNMT sensitized Huh7 cells not only to rapamycin but also to sorafenib treatment both in vitro and in vivo. Therefore, considering the strong relevance between GNMT deficiency and liver disorders as well as the protective role of GNMT against hepatic carcinogenesis, the precise targeting of small molecule compounds that are able to enhance GNMT expression will have important implications for the treatment of HCC.

Preliminary results showed that a small molecule K78 is a potent lead for HCC treatment with the IC50 value of 2.5 μM in Huh7 cells. With the collaboration of the medicinal chemistry team, a comprehensive structure-activity relationship (SAR) study on K78 was performed. In this invention, K-series compounds (K78 derivatives) are synthesized to identify the abilities of K78 and its derivatives to induce a GNMT-promoter reporter activity.

In view of the deficiencies in the prior art, the Applicant have developed the present invention to overcome the deficiencies in the prior art. The summary of the present invention is described below.

SUMMARY OF THE INVENTION

The main object of the present invention is to provide novel GNMT enhancers for treating cancers via increasing GNMT expression in cancer cells.

Therefore, the present invention provides a nicotinohydrazide derivative, a stereoisomer thereof or a pharmaceutically acceptable salt thereof having a structure of formula (I):

(I)

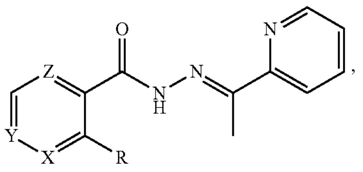

wherein each of X, Y and Z is one of N and CH, at least one of X, Y and Z is CH, at least one of X, Y and Z is N, and R is one of OH and $NH_2$.

In order to synthesize the preferred embodiment of compound having formula (I), the present invention provides a method for preparing a nicotinohydrazide derivative, including the steps of reacting an ethyl nicotinate with a hydrazine hydrate to form a carbohydrazide, and performing a condensation of the carbohydrazide with an acetylpyridine to form N'-(1-(pyridin-2-yl)ethylidene)-2-carbohydrazide (K117) having a structure below:

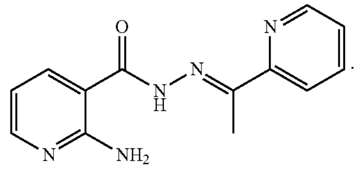

The present invention further provides a pharmaceutical composition including an effective amount of the nicotinohydrazide derivative, its stereoisomer or its pharmaceutically acceptable salt, wherein the nicotinohydrazide derivative has a structure of formula (I).

In a further aspect, the present invention provides a use of the above-mentioned nicotinohydrazide derivative, the stereoisomer thereof or the pharmaceutically acceptable salt thereof for preparing a drug in treating a cancer disease. The nicotinohydrazide derivative has a structure of formula (I), wherein the formula (I) is represented as (I)

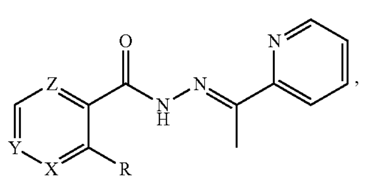

wherein X is one of N and CH, each of Y and Z is CH, and R is one of OH and $NH_2$.

DETAILED DESCRIPTION OF THE PREFERRED EMBODIMENTS

Figure 1:
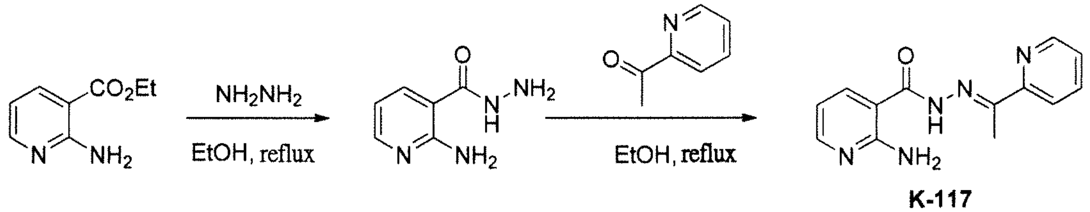
FIG. 1 is a flow chart of synthesizing the preferred embodiment of the nicotinohydrazide derivatives of the present invention.

In accordance with an aspect of the present invention, a nicotinohydrazide derivative, a stereoisomer thereof or a pharmaceutically acceptable salt thereof is provided. In one preferred embodiment, the nicotinohydrazide derivative has a structure of formula (I)

(I)

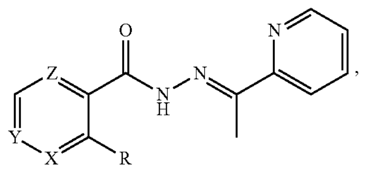

wherein each of X, Y and Z is one of N and CH, at least one of X, Y and Z is CH, at least one of X, Y and Z is N, and R is one of OH and $NH_2$.

The term "nicotinohydrazide derivative" used herein refers to the nicotinohydrazide derivatives, their stereoisomers or their pharmaceutically acceptable salts.

In another aspect of the present invention, a pharmaceutical composition including the nicotinohydrazide derivatives, their stereoisomers or their pharmaceutically acceptable salts is provided. The definitions of the nicotinohydrazide derivatives, their stereoisomers or their pharmaceutically acceptable salts are as described above. Preferably, the pharmaceutical composition further includes at least one of a pharmaceutically acceptable carrier and an excipient.

In a further aspect of the present invention, a method for preparing the preferred embodiment of the nicotinohydrazide derivatives is provided. The method includes the steps of: reacting ethyl nicotinate with hydrazine hydrate to form carbohydrazide, and performing a condensation of the carbohydrazide with acetylpyridine to form N'-(1-(pyridin-2-yl)ethylidene)-2-carbohydrazide (K117) having a structural formula below:

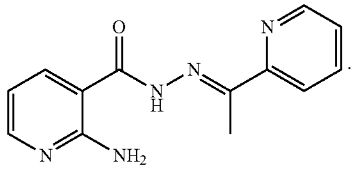 [SMILES: C/C(=N\NC(=O)c1cccnc1N)c1ccccn1]

According to the present invention, the ethyl nicotinate is ethyl 2-aminonicotinate, the carbohydrazide is 2-carbohydrazide, and the acetylpyridine is 2-acetylpyridine.

In a further aspect, the present invention provides a pharmaceutical composition including an effective amount of a nicotinohydrazide derivative, its stereoisomer or its pharmaceutically acceptable salt. The nicotinohydrazide derivative has a structure of formula (I) as described above. Preferably, the pharmaceutical composition further includes at least one of a pharmaceutically acceptable carrier and an excipient.

In a further aspect, the present invention provides a use of the above-mentioned nicotinohydrazide derivative, the stereoisomer and the pharmaceutically acceptable salt thereof for preparing a drug in treating a cancer disease. The nicotinohydrazide derivative has a structure of formula (I), wherein the formula (I) is represented as (I)

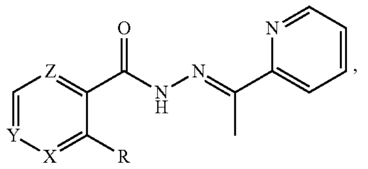

wherein X is one of N and CH, each of Y and Z is CH, and R is one of OH and $NH_2$.

As used herein, the term "cancer" refers to a cellular disorder characterized by the uncontrolled or disordered cell proliferation, the decreased cellular differentiation, the inappropriate ability to invade surrounding tissue, and/or the ability to establish new growth at ectopic sites. The term "cancer" includes, but is not limited to, solid tumors and bloodborne tumors. The term "cancer" includes diseases of skin, tissues, organs, bone, cartilage, blood and blood vessels. The term "cancer" further includes primary and metastatic cancers. Non-limiting examples of cancer in the present invention include the liver cancer, the prostate cancer and the pancreatic cancer. Preferably, the liver cancer is hepatocellular carcinoma.

The pharmaceutical composition of the present invention is used for treating the cancers via enhancing GNMT expression in cancer cells.

EMBODIMENTS

1. Synthesis of Nicotinohydrazide Derivatives

Please refer to FIG. 1, which is a flow chart of synthesizing the preferred embodiment (K117) of the nicotinohydrazide derivatives of the present invention. Ethyl 2-aminonicotinate reacted with hydrazine hydrate to obtain its 2-carbohydrazide. As shown in FIG. 1, 2-carbohydrazide condensed with 2-acetylpyridine to obtain N'-(1-(pyridin-2-yl)ethylidene)-2-carbohydrazide (compound K117).

In another aspect, different ethyl nicotinates are used to synthesize other K-series compounds. Ethyl 2-hydroxynicotinate, ethyl 3-aminoisonicotinate and ethyl 3-aminopyrazine-2-carboxylate respectively reacted with hydrazine hydrate to obtain their respective 2-carbohydrazides. Then, the respective 2-carbohydrazides respectively condensed with 2-acetylpyridine to obtain other compounds having the structure of formula (I). The structures of these compounds are represented as follows:

(I)

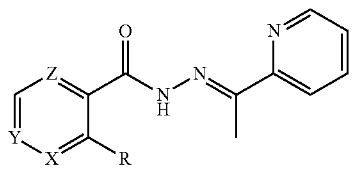

K118 X═N, Y═Z═CH, R═OH

K120 Y═N, X═Z═CH, R═$NH_2$

K121 X═Z═N, Y═CH, R═$NH_2$

2. Cell Culture and Reagents

Human liver cancer cell lines (Huh7 and HepG2), human pancreatic cancer cell line (PANC1) and prostate cancer cell line (PC3) were cultured in Dulbecco's modified Eagle's medium (DMEM) supplemented with 10% fetal bovine serum (FBS) (HyClone, Logan, UT, USA), L-glutamine (2 mM), streptomycin (100 μg/mL), penicillin (100 U/mL) and nonessential amino acids (0.1 mM). Human pancreatic cancer cell line BxPC3 was cultured in the medium of Roswell Park Memorial Institute (RPMI) 1640 with the same supplements as in DMEM. All cell lines were maintained at 37° C. in a humidified $CO_2$ incubator. H7GPL stable cells established by lentiviral-system was grown in DMEM supplemented with 1 μg/mL puromycin. The sorafenib were purchased from Sigma-Aldrich (St Louis, MO, USA).

3. GNMT Induction Capacity Assay

A −1812/+14 GNMT promoter-luciferase reporter cell line H7GPL was constructed. For the primary analysis, H7GPL cells seeded in 96-well plates were treated with individual drugs of 10 μM for 24 hours and then were lysed for the luciferase activity assay using Luciferase Assay System (Promega, Madison, WI, USA). Then, the secondary analysis was performed using the compounds with different doses. The same confirmed hits were used for cytotoxicity by using alamarBlue® reagent (AbD serotec, Oxford, UK). The cytotoxicity was measured according to the manufacturer's recommendation. Top hits were used for further studies.

4. Cell Viability and Colony Formation Assay

Huh7, HepG2, PANC1, PC3, and BxPC3 cells were seeded in 96-well plates for 24 hours and exposed to the drugs with various concentrations. AlamarBlue® was added in to the cells and further incubated for 4 hours to assess the cytotoxic effect of the tested drugs. Blank wells (without cells) containing the same amount of test substances were used for background subtraction, and the relative number of viable cells were represented as the percentage of the mean of the relative solvent controls. AlamarBlue® assay (AbD Serotec, Oxford, UK) was used to assess cell viability according to the manufacturer's instructions.

5. Immunoblotting

Cells or xenograft tumors were harvested for lysate preparation by using RIPA buffer containing protease inhibitor cocktail (Roche Molecular Biochemicals) and phosphatase inhibitors (10 mM $Na_3VO_4$, 1 mM NaF, 5 mM NaPPi). Protein concentrations were quantified by Bio-Rad Protein Assay (Bio-Rad) and immunoblotting was carried out as previous description (Yen et al., 2012). Anti-MYC (D84C12, Cell Signaling Technology), anti-GNMT (YMAC-Bioteck) and anti-β-actin (AC-15, Sigma-Aldrich) antibodies were used according to the descriptions in manufacturer's instructions.

6. Quantitative Real-Time PCR (qRT-PCR)

RNA was isolated by using Trizol reagent (Life Technologies) according to the manufacturer's protocol. Cellular RNA was reverse transcribed into complementary DNA using a SuperScript II RNase H-Reverse Transcriptase Kit (Life Technologies). PCR reactions were carried out using a Super Script II Reverse Transcriptase Kit (Invitrogen Inc., Carlsbad, CA, USA) on an Applied Biosystems Step-One-plus real-time PCR system (Applied Biosystems, Foster City, CA, USA). The mRNA level of TATA-box binding protein (TBP) was used as an internal control. The primer pairs used for qRT-PCR were:

TBP forward: SEQ ID NO: 1,
 reverse: SEQ ID NO: 2,
MYC forward: SEQ ID NO: 3,
 reverse: SEQ ID NO: 4,
p21 forward: SEQ ID NO: 5,
 reverse: SEQ ID NO: 6,
p27 forward: SEQ ID NO: 7,
 reverse: SEQ ID NO: 8,
GNMT forward: SEQ ID NO: 9, and
 reverse: SEQ ID NO: 10.

7. Plasmids and Transfections

Plasmids for lentivirus production (pCMV-ΔR8.91 and pMD.G), shRNAs for MYC (MYC-lentiviral shRNA, SEQ ID NO: 11) and control plasmid for the RNA interference (pLKO.1-shLacZ) were obtained from the National RNAi Core Facility (Academia *Sinica*, Taipei, Taiwan). The vector control plasmid and pcDNA-MYC plasmid for overexpression experiments were provided by Dr. Shih-Ping Liu (China Medical University, Taichung, Taiwan). The *Renilla* luciferase control reporter vector (Promega, Madison, WI, USA) was used for standardizing transfection efficiency. Plasmid DNAs were transfected by using TurboFect Reagent (Fermentas, Hanover, MD) and Lipofectamine 3000 (Life Technologies, Mulgrave, Australia) according to the manufacturers' recommendations.

8. Xenograft Assay

All animal experiments were reviewed and approved by the Institutional Animal Care and Use Committee of Kaohsiung Medical University, and performed in accordance with relevant guidelines. Five to six-week-old male NOD-SCID mice were subcutaneously injected with Huh7 cells ($1\times10^6$) in the right flank. Upon detection of palpable tumor, mice were randomly grouped and treated with 300 mpk, 100 mpk or 25 mpk of LKY4606D or KYT5397 and drug vehicle orally every day for 28 days. For K117, doses of 10 mpk and 25 mpk were used. For Sorafenib, dose of 25 mpk was used. Tumor growth was monitored (every day or three times per week) by measuring the length (L) and the width (W) of the tumor using Vernier caliper. Tumor volume (TV) was calculated by using the formula: volume=$(L\times W^2)/2$. All drugs were dissolved in 0.5% carboxymethyl cellulose sodium salt.

9. Statistical Analysis

Statistical analyses were performed using MS excel and Graph Pad Prism 5.0 software. To compare various groups, P-values were determined by student's two-sided t-tests and considered to be statistically significant at $P<0.05$.

Results

1. Identification of GNMT Inducer

Figure 2A:
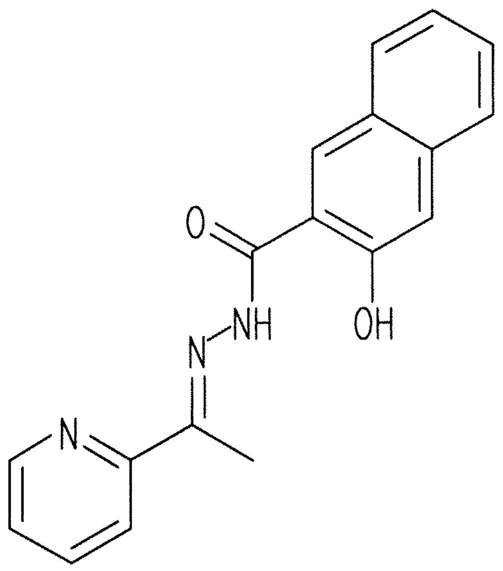
FIG. 2A shows the structure of K78.
Figure 2B:
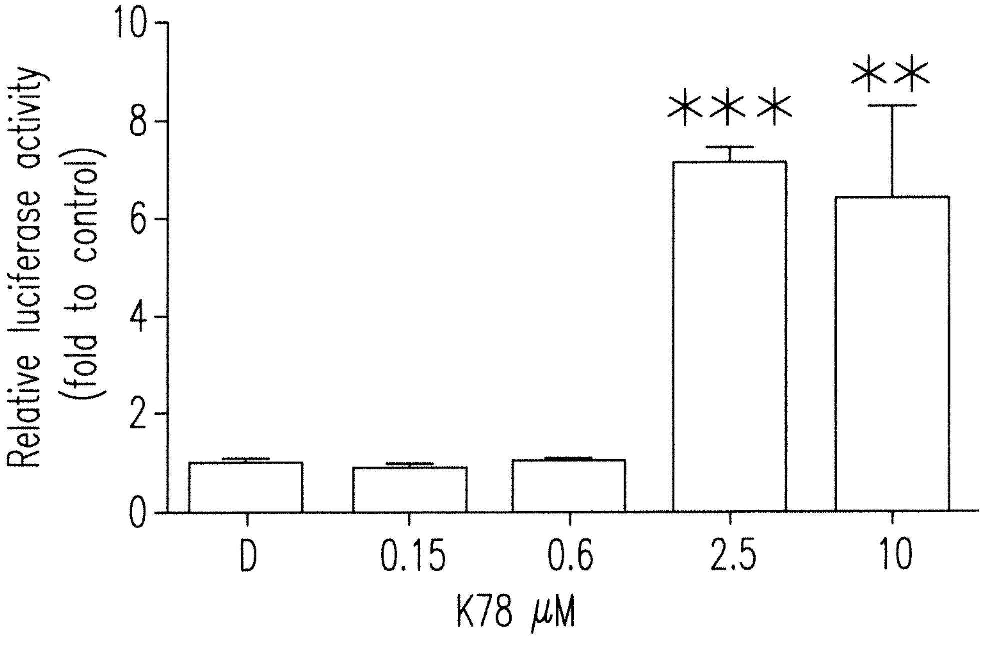
FIGS. 2B~2D show the effects of K78 on the expression of GNMT.
Figure 2C:
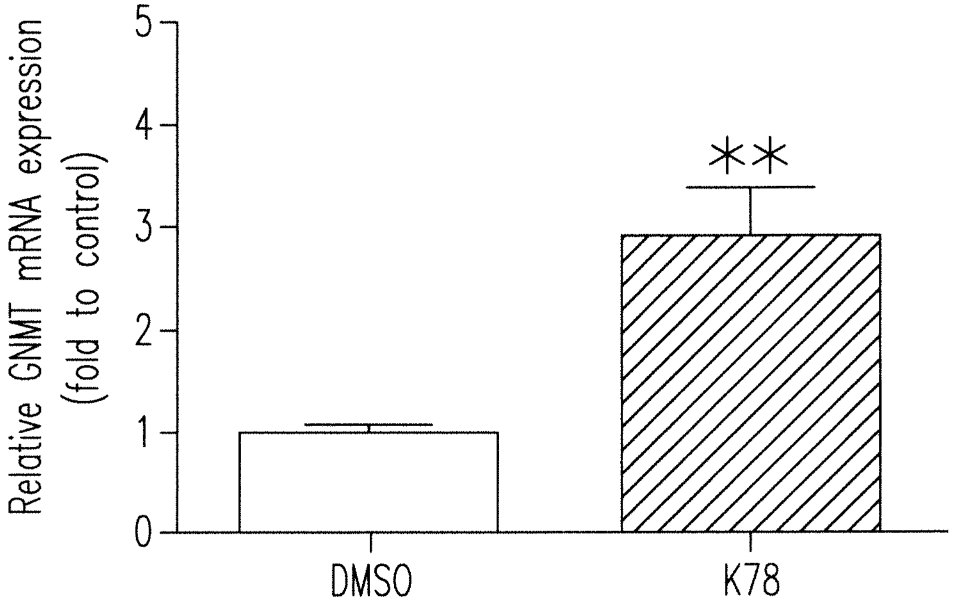
Figure 2D:
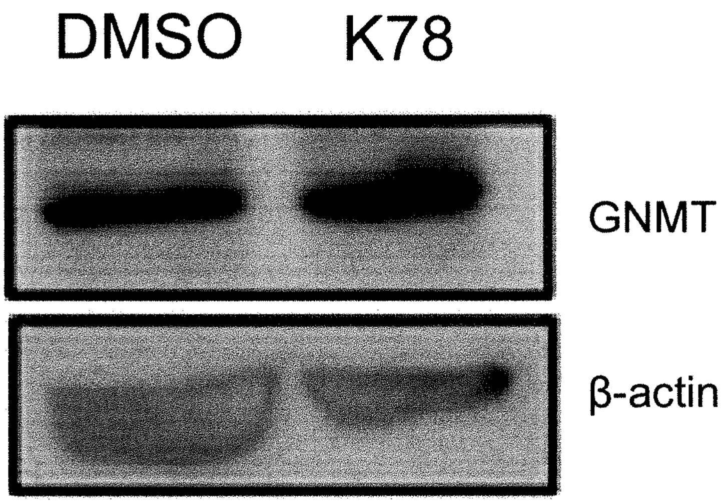

Preliminary studies showed that a naphthohydrazide derivative, K78, whose structure is shown in FIG. 2A is a potent lead for HCC treatment. As shown in FIG. 2B, K78 showed dose-dependent induction of luciferase activity and was selected as a potential candidate for inducer of reporter gene expression. To confirm whether K78 enhances endogenous GNMT expression, GNMT mRNA and protein levels in Huh7 cells were examined. As shown in FIGS. 2C and 2D, K78 up-regulated endogenous GNMT expression at mRNA level (FIG. 2C) and protein level (FIG. 2D) in Huh7 cells.

2. The Anti-HCC Effect of K78 In Vitro and In Vivo

Figure 3A:
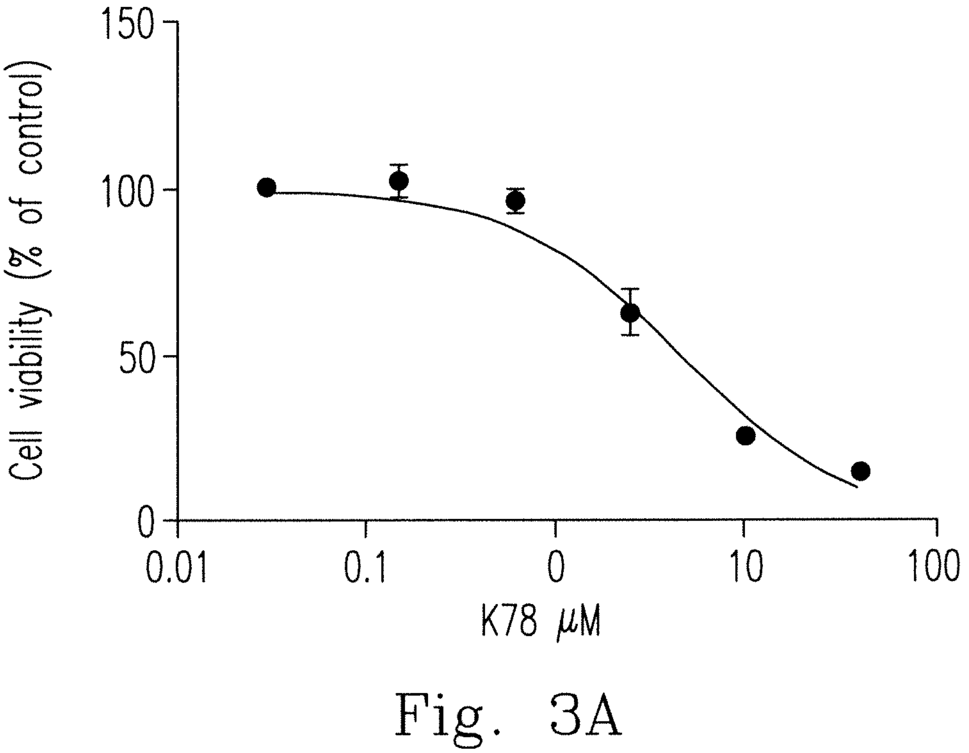
FIGS. 3A~3D show the effects of K78 on inhibiting liver cancer cell's growth in vitro and in vivo.
Figure 3B:
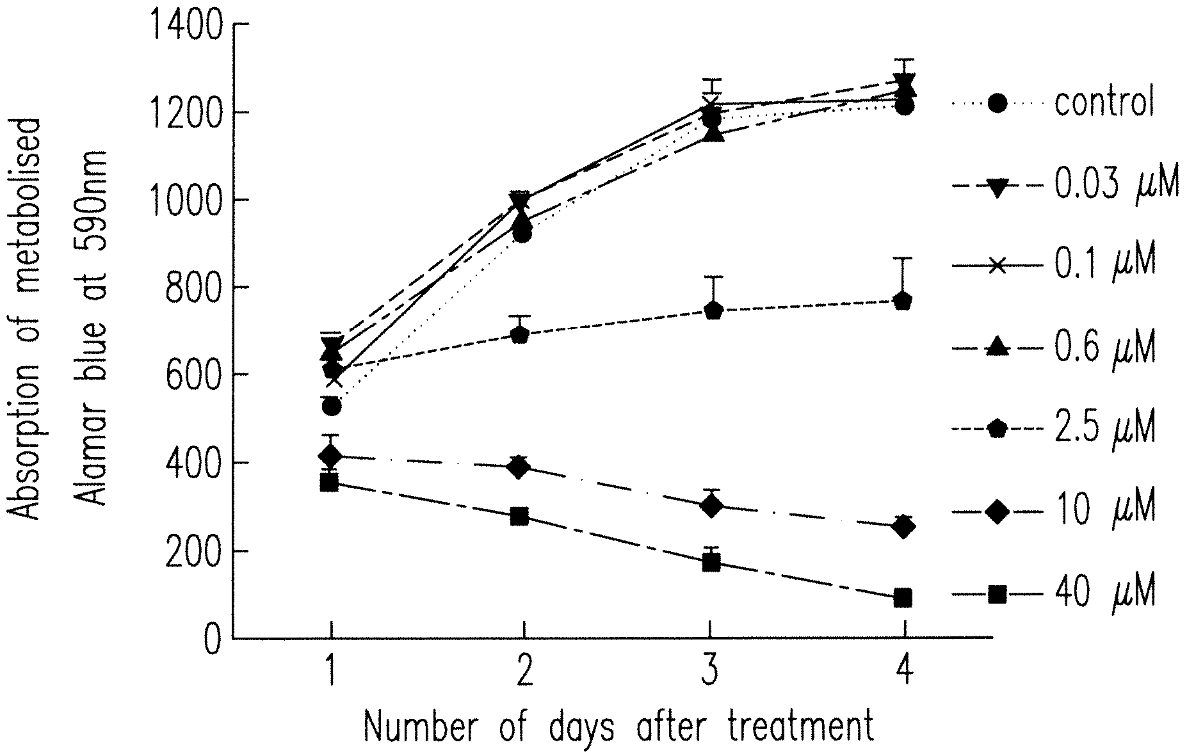
Figure 3C:
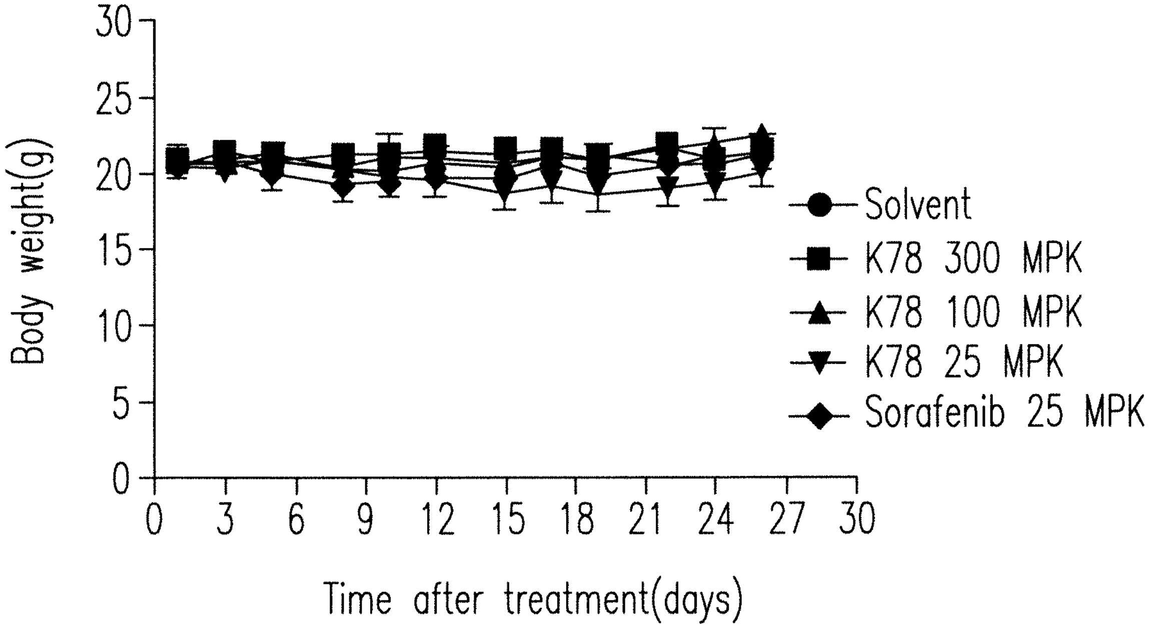
Figure 3D:
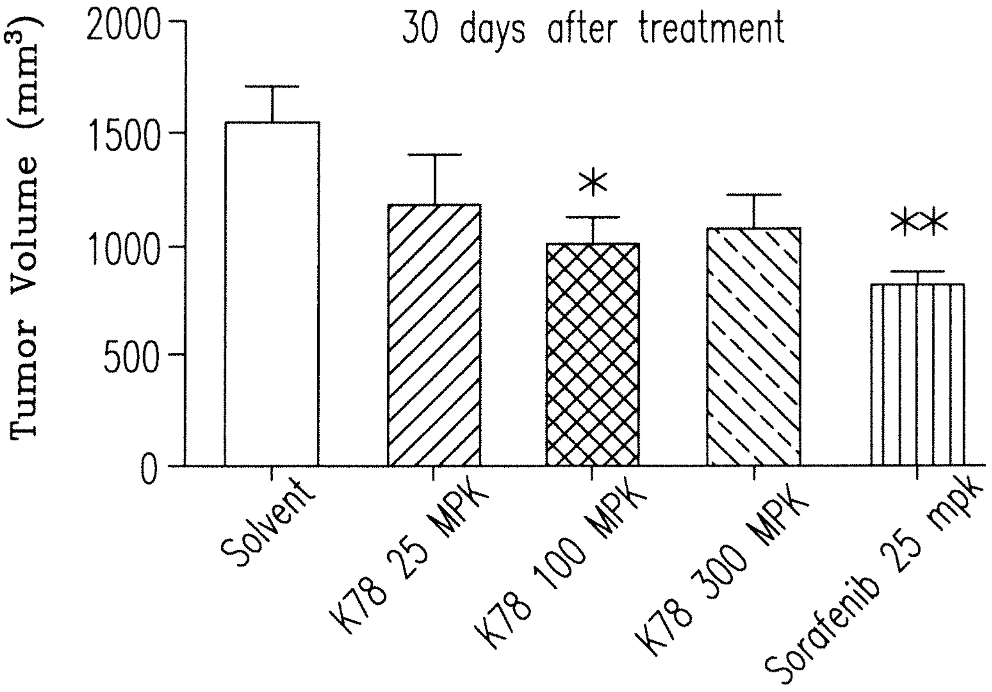

To determine the therapeutic potential of K78 against HCC, the inhibitory effect of K78 on the growth of Huh7 cells was firstly evaluated. K78 suppressed the proliferation of Huh7 cells in a dose-dependent manner after 72 hours of treatment (FIG. 3A). Subsequently, after exposing to K78 for 24, 48, 72 and 96 hours, the proliferation of Huh7 cells were significantly inhibited in a time-dependent manner (FIG. 3B). Next, studies on a xenogeneic model were conducted in the present invention using Huh7 cells. Tumor-bearing nude mice were treated orally with solvent, K78 25 mpk, K78 100 mpk and K78 300 mpk. Sorafenib was chosen as a comparison control because it is an FDA approved drug for HCC. There was no evidence of toxicity on body weight in all groups (FIG. 3C). As shown in FIG. 3D, K78 inhibits tumor growth in this model in comparison with the solvent control. However, sorafenib has the most significant difference. Taken together, these results provide strong evidences for the anti-HCC ability of K78 using in vitro and in vivo models.

Figure 4A:
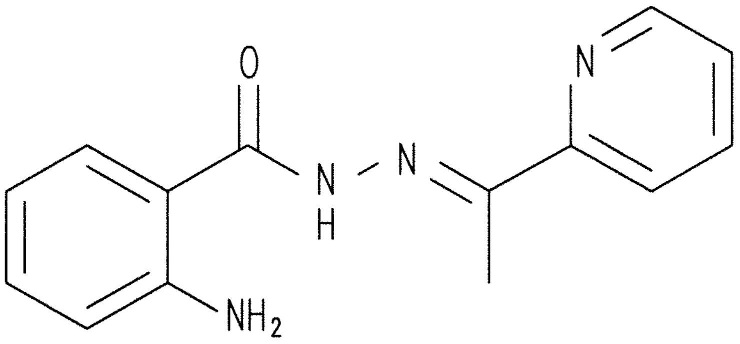
FIG. 4A shows the structure of K102.
Figure 4B:
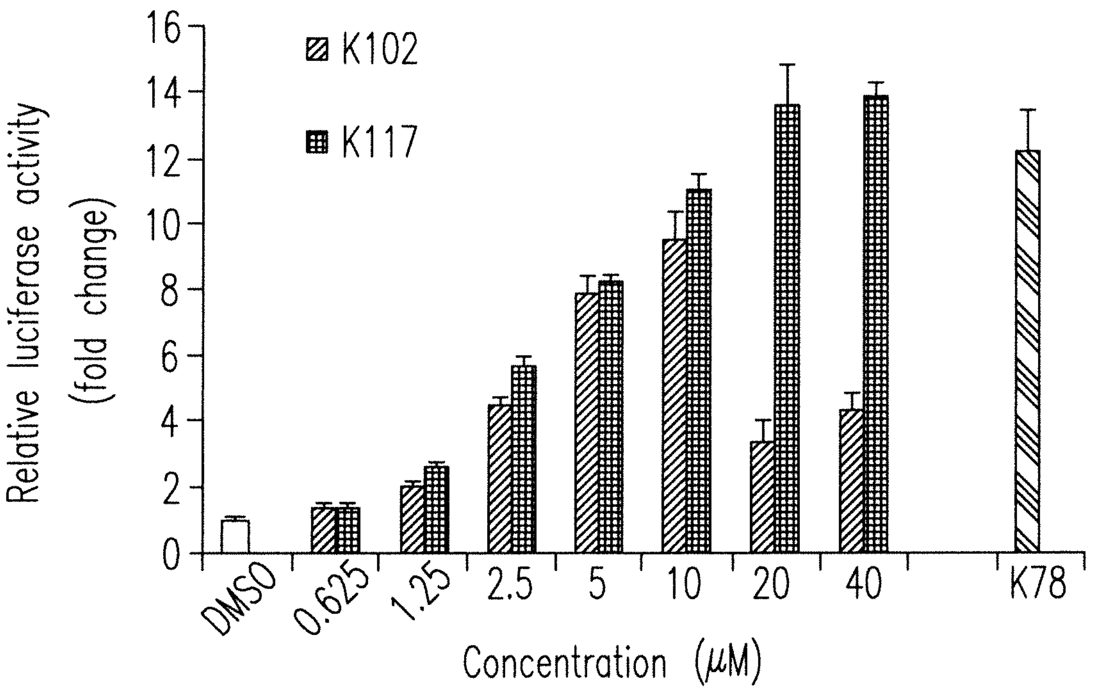
FIGS. 4B~4D show the effects of the compounds K117 and K102 on the expression of GNMT.
Figure 4C:
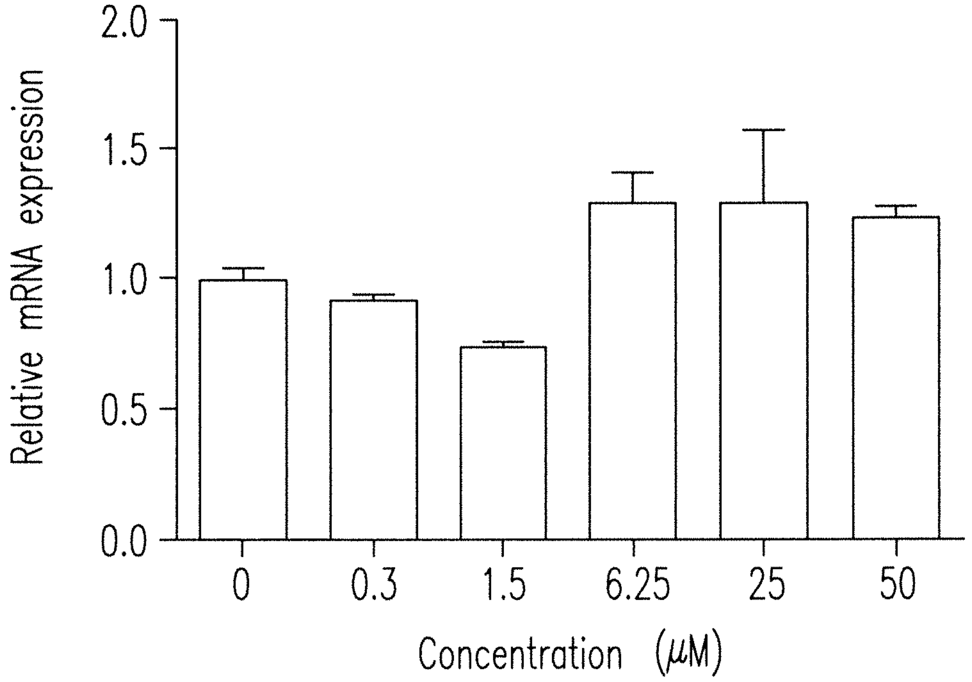
Figure 4D:
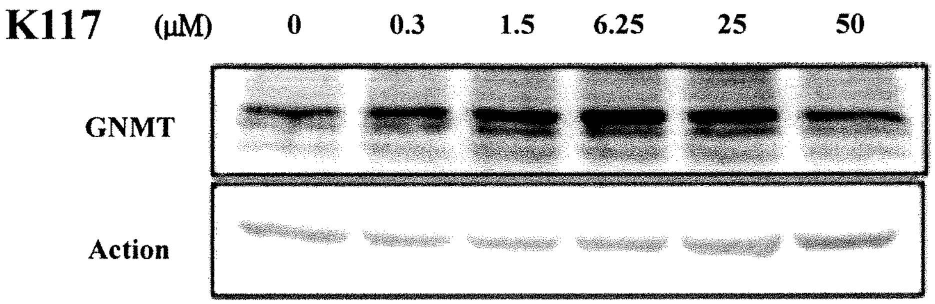

By performing structure-activity relationship (SAR) study, we identified more potent HCC inhibiting drugs with ability to enhance GNMT expression. K117 and K102 (K78 derivatives) were more effective than K78 in inducing GNMT expression. The structure of K102 is shown in FIG. 4A. Furthermore, K117 and K102 induced GNMT promoter activity in a dose-dependent manner (FIG. 4B). Then, the most potent inducer K117 was chosen for further studies and induced GNMT mRNA as well as protein expressions in Huh7 cells (FIGS. 4C and 4D).

By performing structure-activity relationship (SAR) study, as shown in Table 1, K-series compounds (GNMT inducers) were synthesized by different ethyl nicotinates. Table 1 shows GNMT induction capacity of K-series compounds.

TABLE 1

The induction capacity (Relative Luciferase Activity) of selected compounds

| Drug code | | Relative Luciferase Activity 2.5 μM | 5.0 μM | 10 μM |
|---|---|---|---|---|
| K-117 | 23a | 6.52 ± 0.12 | | 10.36 ± 0.35 |
| K-118 | 23b | 1.51 ± 0.05 | | 1.43 ± 0.04 |
| K-120 | 23c | 4.54 ± 0.24 | | 7.78 ± 0.75 |
| K-121 | 23d | 1.18 ± 0.07 | | 1.16 ± 0.16 |
| K78 | | 4.42 ± 0.79 | 6.23 ± 0.19 | 10.63 ± 1.08 |

3. K117 Inhibits Liver Cancer Cells In Vitro and In Vivo

Figure 5A:
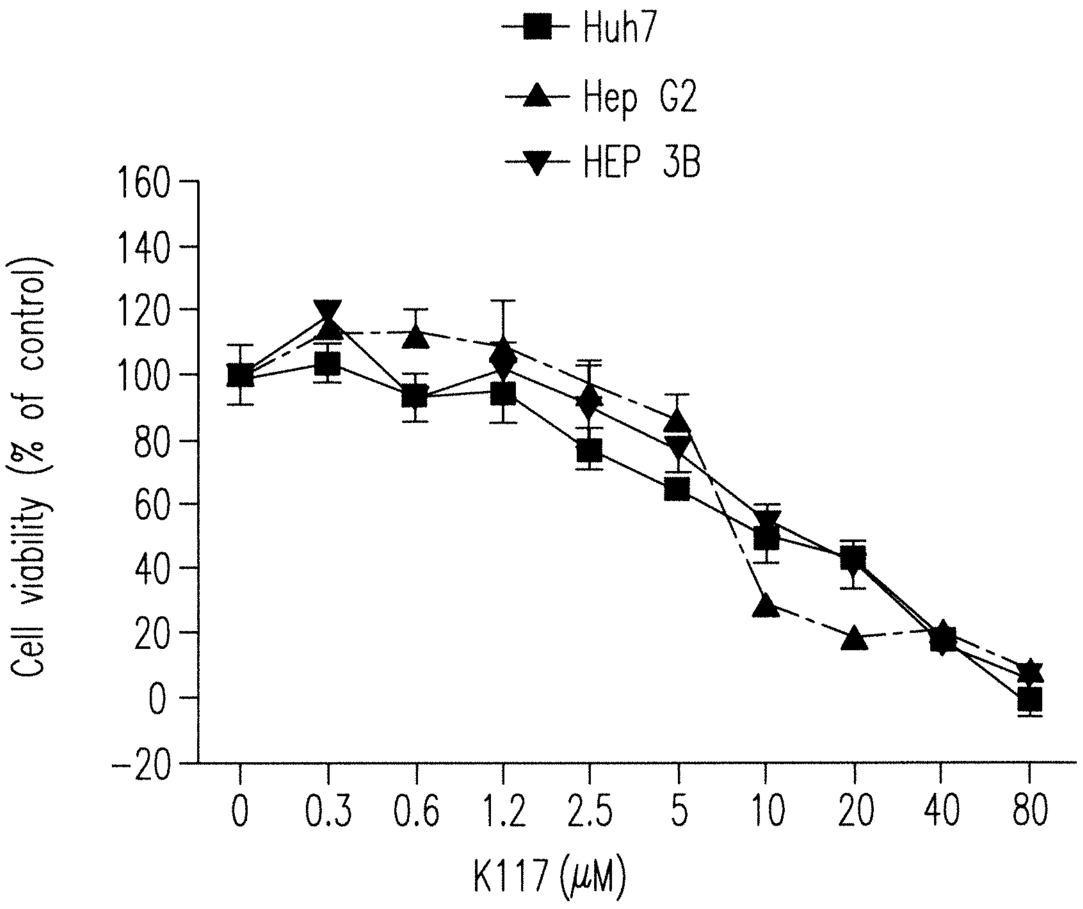
FIGS. 5A~5F show the effects of K117 on inhibiting liver cancer cell's growth in vitro and in vivo.
Figure 5B:
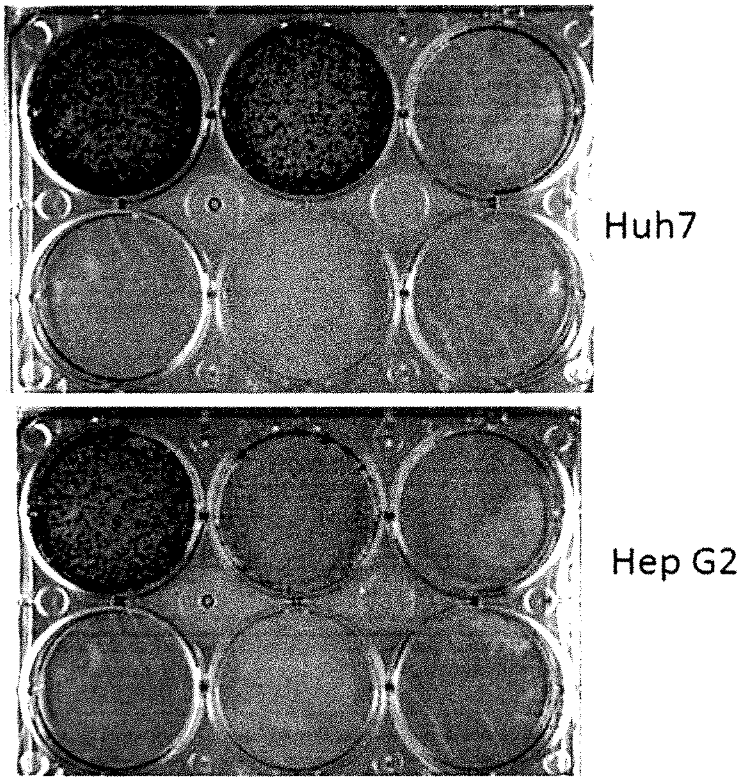
Figure 5C:
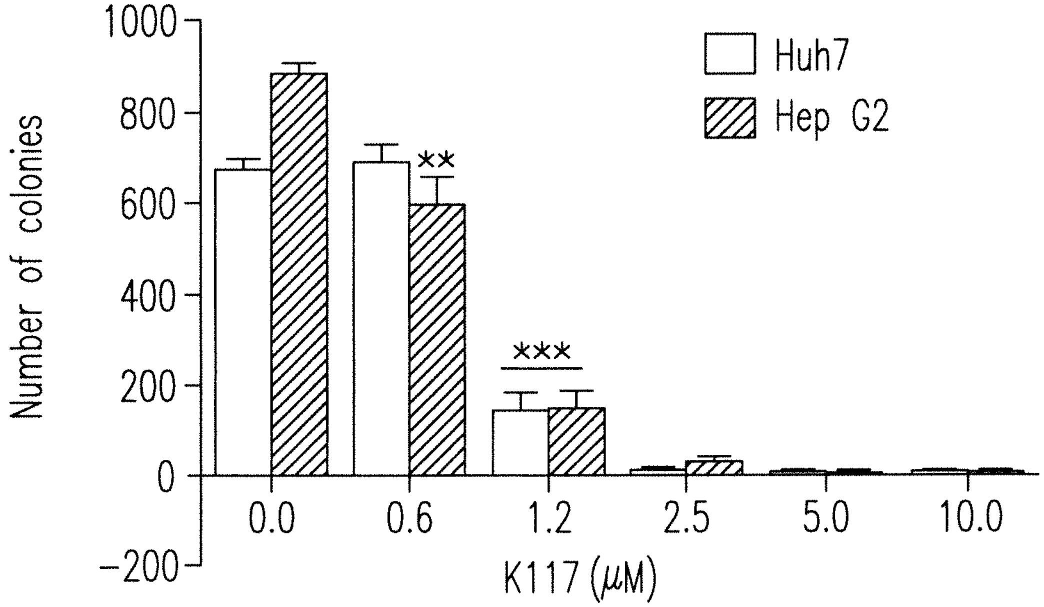

Next, we analyzed the effect of K117 on cell proliferation in different liver cancer cell lines (including Huh7, Hep3B, and HepG2). Results showed that K117 inhibited proliferation of all tested liver cancer cells in a dose-dependent manner (FIG. 5A). Furthermore, K117 reduced the colony formation of Huh7 and HepG2 cells in a dose-dependent manner (FIGS. 5B and 5C). To further evaluate the anti-tumor effect of K117 in vivo, Huh7 cells were injected subcutaneously into nude mice as described above. These mice were then randomly grouped and treated with solvent, K117 25 mpk, K117 10 mpk and Sorafenib 25 mpk (as a comparison control).

Figure 5D:
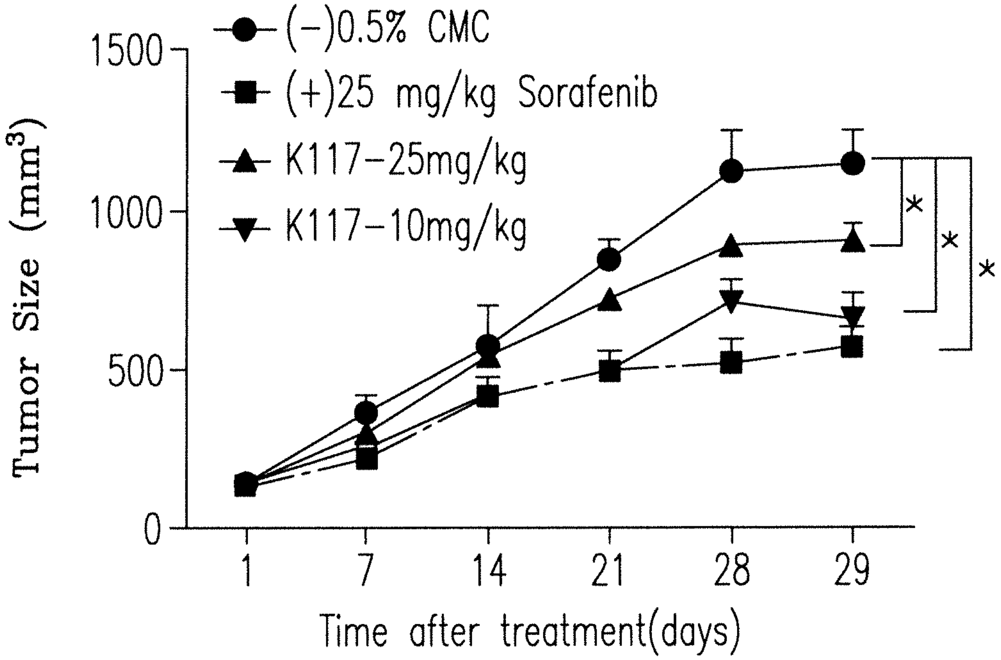
Figure 5E:
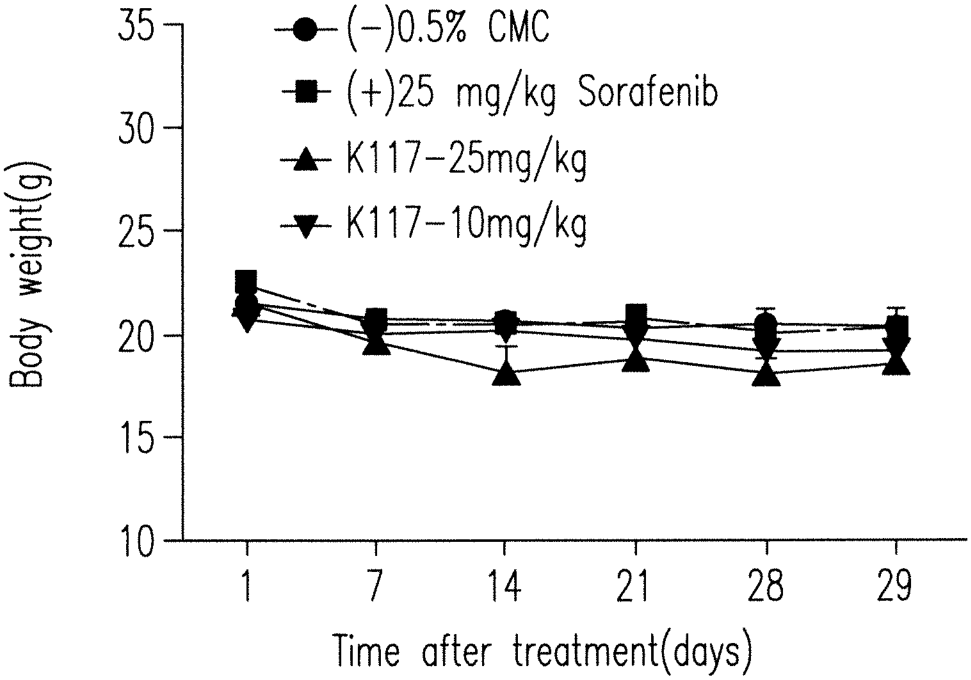
Figure 5F:
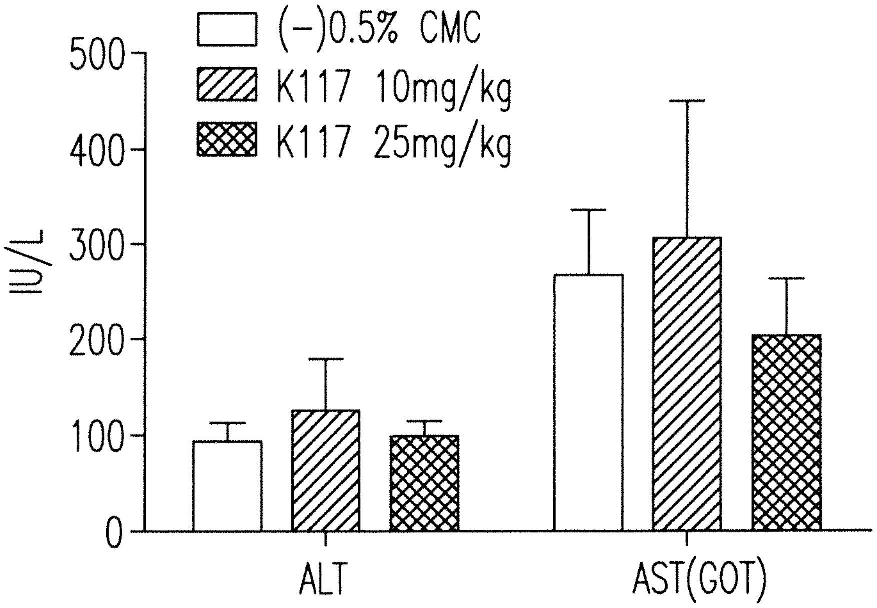

As shown in FIG. 5D, a significant tumor growth reduction was observed in the K117 treatment groups, when compared with the control group. Moreover, K117 at the lower dose of 10 mpk showed the same effect as Sorafenib 25 mpk. In addition, K117 treatment produced no severe adverse events as monitored by animal survival, body weight and liver function tests, but there is no significant difference among all groups (FIGS. 5E and 5F). Altogether, these results provide strong evidence for the tumor growth-inhibiting activity and tolerability of K117 in vitro and in vivo.

4. GNMT Acts as a Tumor Susceptibility Gene (TSG) in Prostate Cancer and Pancreatic Cancer It has been reported that GNMT expression in normal prostatic and benign prostatic hyperplasia tissues was abundant whereas it was reduced in 82.2% of the prostate cancer tissues. This suggested that GNMT is a tumor susceptibility gene for the prostate cancer.

It is found in many cancers including pancreatic cancer that hypermethylation is utilized to silence gene. In such condition, GNMT downregulation may aid the availability of the methyl donor SAM to perform gene silencing. Previously, GNMT was found significantly down-regulated in the pancreatic cancer, and the secondary tumor from the pancreatic cancer often aim at liver. In this regard, it is similar to HCC that GNMT may be a TSG in the pancreatic cancer, and the re-activation of this down-regulated TSG in the pancreatic cancer would be a therapeutic regimen. Table 2 shows $IC_{50}$ (μM) of the pancreatic and prostate cancer cell-lines. It indicates that the induction of GNMT inhibits the growth of cancer cells.

TABLE 2

IC$_{50}$ (μM) of the pancreatic and prostate cancer cell-lines.

| | Cancer type | | | |
| --- | --- | --- | --- | --- |
| | Pancreas | | Prostate | |
| Drug | BxPC3 | PANC1 | DU145 | PC3 |
| K117 | 1.2 | 2.2 | 40.8 | 15.3 |

5. Mechanism of k78-Series GNMT Inducers in HCC

Figure 6A:
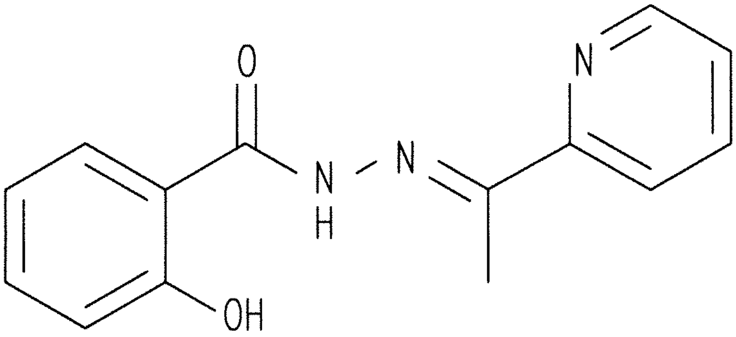
FIG. 6A shows the structure of K90.
Figure 6B:
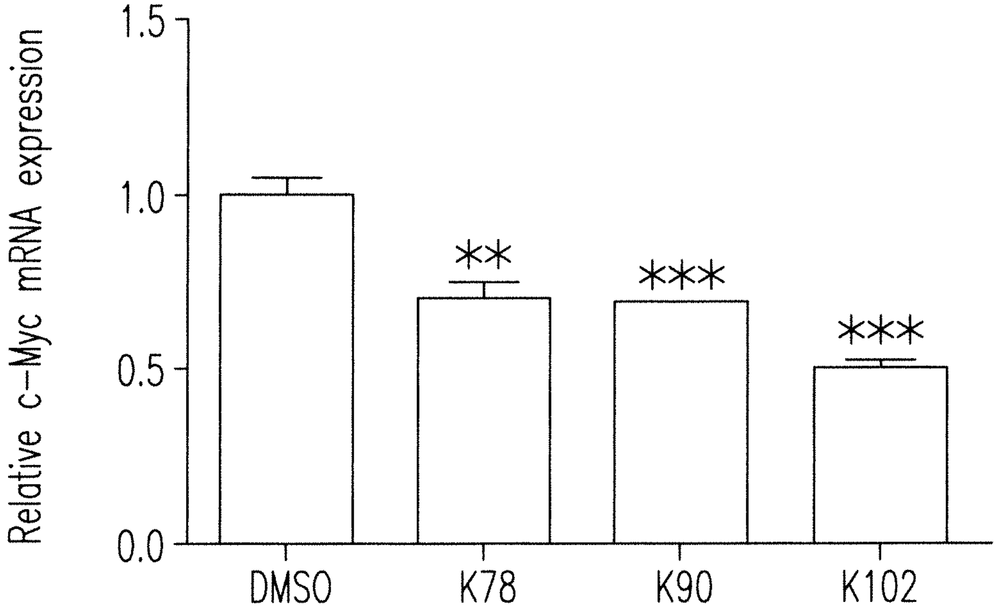
FIGS. 6B~6H show the effects of GNMT-inducing compounds on Myc expression.
Figure 6C:
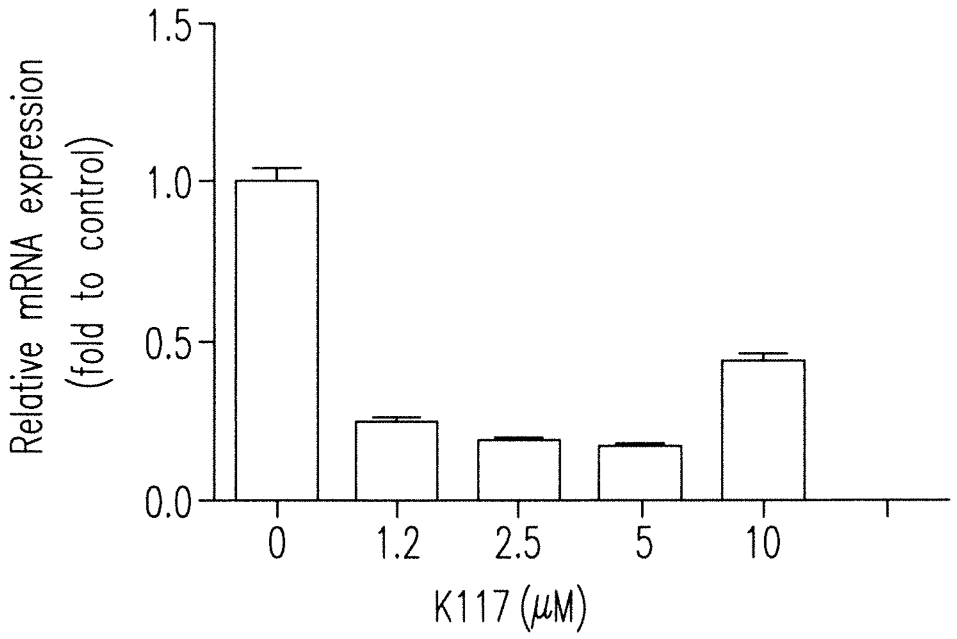
Figure 6D:
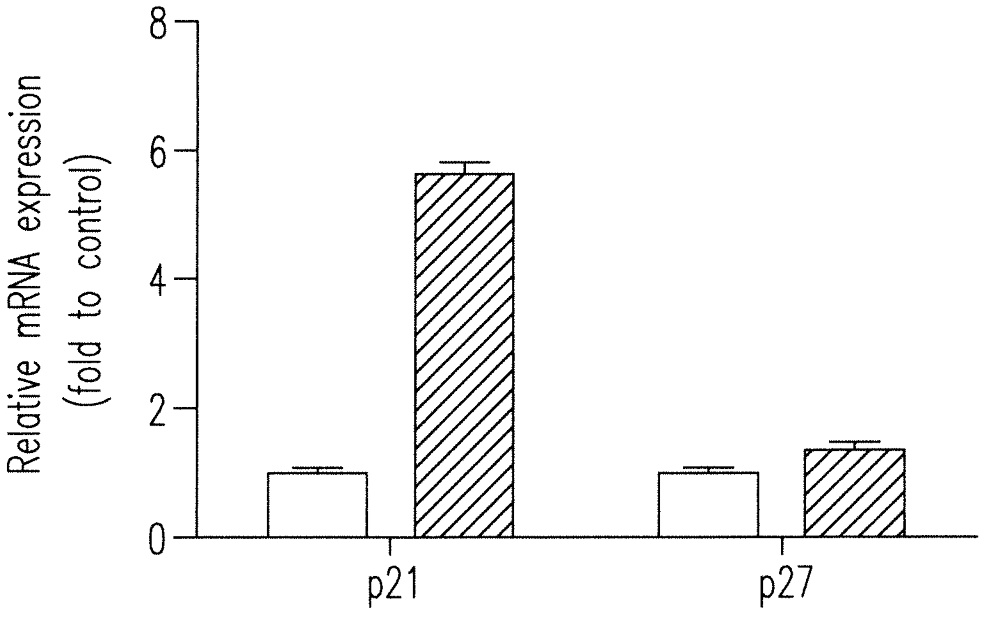
Figure 6E:
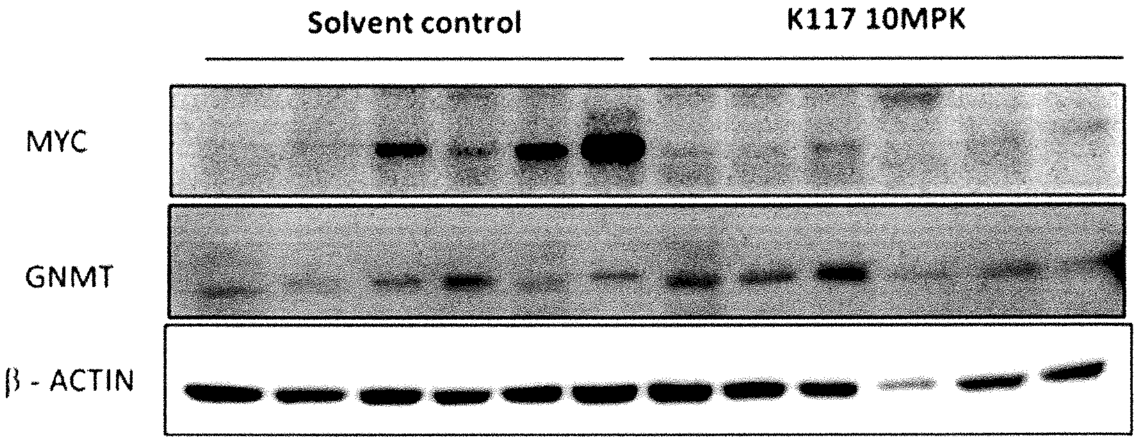
Figure 6F:
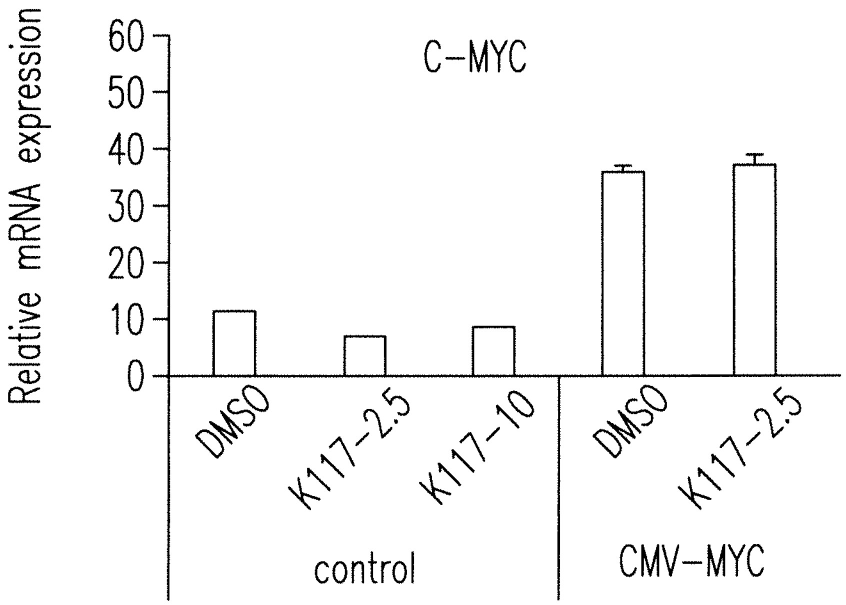
Figure 6G:
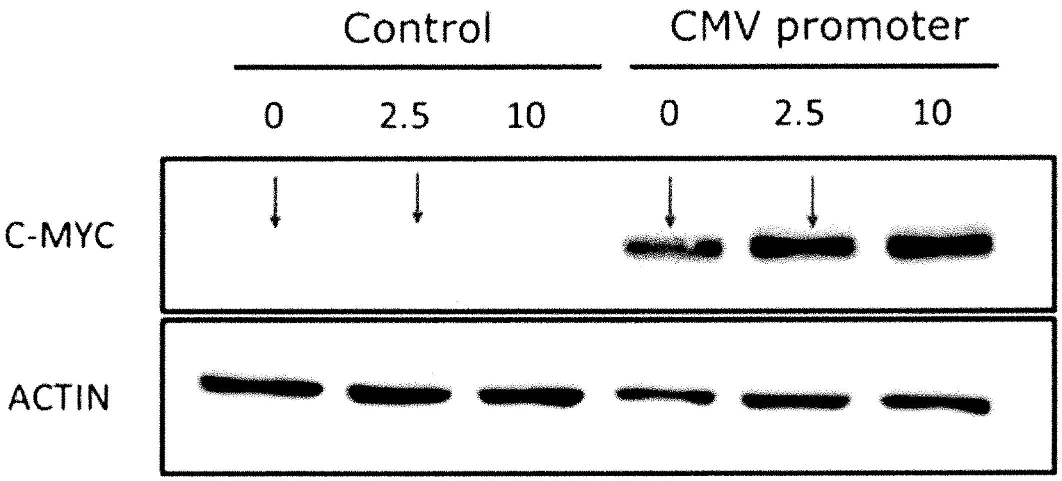
Figure 6H:
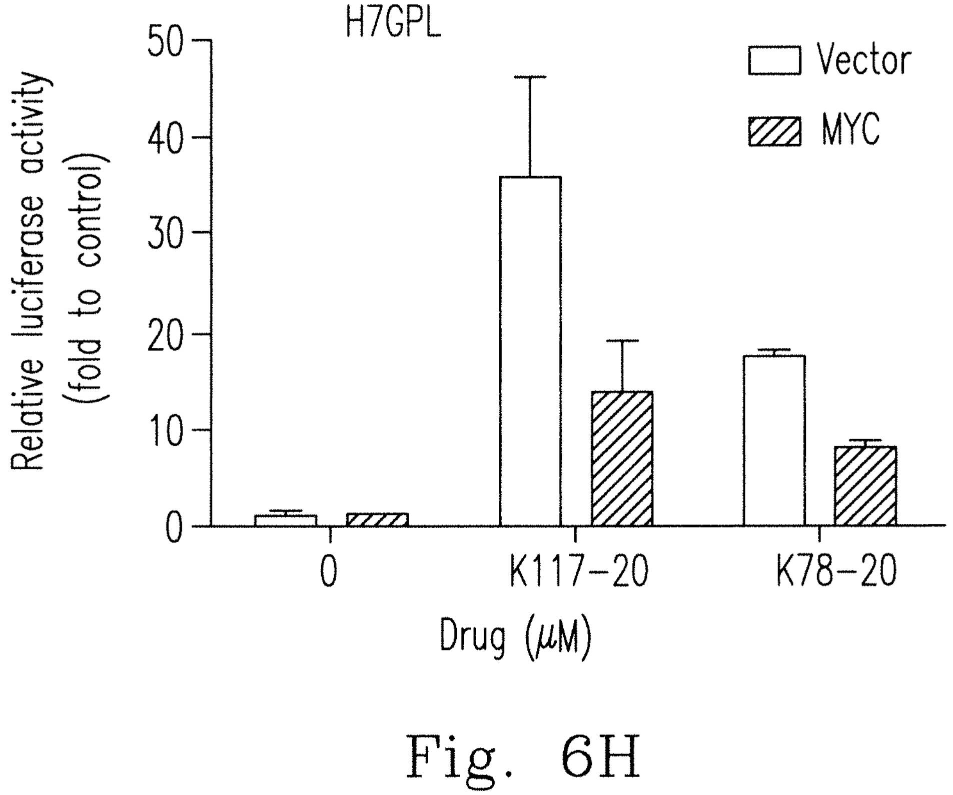

Next, the mechanism by which K78 enhances GNMT expression and inhibits liver cancer cell proliferation was explored in the present invention. It is known that the GNMT inducer drug 1,2,3,4,6-penta-O-galloyl-Beta-D-glucopyranoside (PGG) enhanced GNMT expression through MYC downregulation in the pathogenesis of liver cancer. Therefore, in order to determine whether K78-series compounds also exert their effect through MYC inhibition in HCC, the effects of K78-series compounds (K78, K90 and K102) treating on mRNA expression of MYC in Huh7 cells were examined in the present invention. The structure of K90 is shown in FIG. 6A. As shown in FIG. 6B, all K78-series compounds (K78, K90 and K102) inhibit MYC mRNA expression in Huh7 cells. It is further showed that K117 suppressed c-Myc mRNA expression dose-dependently (FIG. 6C). Moreover, the effect of K117 on MYC function was evaluated in the present invention by analyzing the expression of MYC target genes after K117 treatment. Consistent with MYC inhibition, K117 treatment increased the mRNA expressions of p21 and p27 in Huh7 cells (FIG. 6D). Consistent with in vitro results, MYC protein expression was reduced in Huh7 xenograft tumors of mice treated by K117 (FIG. 6E). These results demonstrated that K78-series compounds are MYC inhibitors, which suppress MYC expression in HCC cells. It has been shown that PGG inhibits MYC gene expression and enhances the degradation of the MYC protein through mechanisms irrelevant to proteasome as well as calpain. To explore the operation of this same mechanism in K78-series compounds, the present invention examined whether ectopic expression of MYC would rescue the MYC mRNA and protein suppressions induced by K117 in Huh7 cells. Interestingly, the ectopic expression of MYC was able to rescue the MYC mRNA and protein suppression induced by K117 in Huh7 cells (FIGS. 6F and 6G). In addition, the results of induction showed that overexpression of MYC reverts the GNMT promoter activity in K117-induced H7GPL-1 cells (FIG. 6H). Collectively, K78-series compounds suppressed MYC transcription and enhanced GNMT expression.

The present invention may be modified in any way by those skilled in the art without departing from the scope of the appended claims.

The invention claimed is:

1. A nicotinohydrazide compound of formula (I) or a pharmaceutically acceptable salt thereof:

(I)

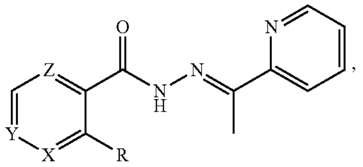

, wherein the nicotinohydrazide compound of formula (I) is selected from one of the following:

(i) X is N, and both Y and Z are CH; (ii) Y is N, and both X and Z are CH; and (iii) both X and Z are N, and Y is CH, and R is $NH_2$.

2. A method for preparing a nicotinohydrazide compound, comprising steps of:

reacting an ethyl 2-aminonicotinate with a hydrazine hydrate in an alcohol solution to form a 2-carbohydrazide; and performing a condensation of the 2-carbohydrazide with a 2-acetylpyridine in the alcohol solution to form an N'-(1-(pyridin-2-yl)ethylidene)-2-carbohydrazide having a structure below:

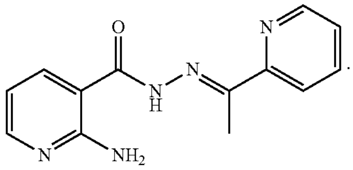 [SMILES: C/C(=N\NC(=O)c1cccnc1N)c1ccccn1]

.

3. A method for treating a cancer disease, comprising:

administering a pharmaceutical composition comprising an effective amount of a nicotinohydrazide compound of formula (I) or a pharmaceutically acceptable salt thereof (I)

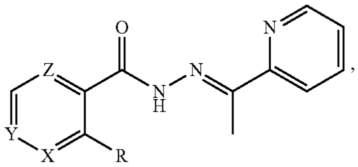

, to a subject suffering from the cancer disease, wherein X is one of N and CH, both Y and Z are CH, and R is $NH_2$, and the cancer disease is one selected from a group consisting of a liver cancer, a prostate cancer and a pancreatic cancer.

4. The method according to claim 3, wherein the liver cancer is hepatocellular carcinoma.

5. The method according to claim 3, wherein the pharmaceutical composition further comprises at least one of a pharmaceutically acceptable carrier and an excipient.

* * * * *